United States Patent
Yang et al.

(10) Patent No.: US 8,597,241 B2
(45) Date of Patent: Dec. 3, 2013

(54) RETAINED NEEDLE STRUCTURE OF NON-RADIAL OPERATING STRUCTURE

(76) Inventors: Chang-Ming Yang, Miaoli (TW); Chun-Mei Chou, Miaoli (TW)

(*) Notice: Subject to any disclaimer, the term of this patent is extended or adjusted under 35 U.S.C. 154(b) by 604 days.

(21) Appl. No.: 12/389,662

(22) Filed: Feb. 20, 2009

(65) Prior Publication Data
US 2009/0216199 A1 Aug. 27, 2009

Related U.S. Application Data

(63) Continuation-in-part of application No. 10/569,623, filed on Feb. 27, 2006, now abandoned.

(51) Int. Cl.
*A61M 5/00* (2006.01)
*A61M 5/178* (2006.01)

(52) U.S. Cl.
USPC .................. 604/110; 604/164.04

(58) Field of Classification Search
USPC ......... 604/110, 164, 167, 169, 192, 198, 263, 604/264, 269, 164.01–164.13
See application file for complete search history.

(56) References Cited

U.S. PATENT DOCUMENTS

| | | | |
|---|---|---|---|
| 4,850,961 A * | 7/1989 | Wanderer et al. | 604/508 |
| 4,917,669 A * | 4/1990 | Bonaldo | 604/192 |
| 5,000,740 A * | 3/1991 | Ducharme et al. | 604/162 |
| 5,102,394 A * | 4/1992 | Lasaitis et al. | 604/164.08 |
| 5,273,540 A * | 12/1993 | Luther et al. | 604/110 |
| 5,429,613 A * | 7/1995 | D'Amico | 604/198 |
| 5,456,668 A * | 10/1995 | Ogle, II | 604/110 |
| 5,520,654 A * | 5/1996 | Wahlberg | 604/164.08 |
| 5,651,772 A * | 7/1997 | Arnett | 604/164.01 |
| 5,951,515 A * | 9/1999 | Osterlind | 604/110 |
| 5,954,698 A * | 9/1999 | Pike | 604/167.03 |
| 7,291,128 B2 * | 11/2007 | Rossi et al. | 604/110 |
| 2004/0116863 A1 * | 6/2004 | Yang et al. | 604/164.01 |

* cited by examiner

*Primary Examiner* — Kevin C Sirmons
*Assistant Examiner* — William Carpenter
(74) *Attorney, Agent, or Firm* — Osha Liang LLP (57) ABSTRACT

A retained needle structure of a comprises a syringe needle with one or more fastening portion, a catheter with a cannula having a flexible tube, as well as a syringe cover with an aperture and gliding portion. The syringe needle has an inserting portion which is axially operated by users to enhance safety practice in clinical use. First design is the sliding slot has a deflected slant portion at the distal end. When the fastening portion is at the rear end of sliding slot, the injection needle is already inside of syringe cover. At the same point, body of the syringe needle is deflected laterally from the center of the syringe cover.

The second design is used the levering effect from gravity of syringe cover. When the fastening portion is at the rear end of sliding slot, the syringe cover is vertically rotated from the original center of the syringe cover.

10 Claims, 6 Drawing Sheets

RETAINED NEEDLE STRUCTURE OF NON-RADIAL OPERATING STRUCTURE

The present invention is a continuation-in-part (CIP) of U.S. application Ser. No. 10/569,623, and claims the priority filing date of Feb. 27, 2006. In the claims, claim 1 of the present application corresponds to both claim 1 and claim 3 of patent application; claim 4 corresponds to both claim 28 and claim 29 of patent application; claim 8 is a newly added claim; other claims in the present application are dependent claims. This invention relates to a user-friendly improvement on a retained needle structure, and particularly to a retained needle structure which is axially operated.

FIELD OF THE INVENTION

Description of the Prior Art

The present invention is an improvement on U.S. Pat. No. 5,954,698, in which a catheter hub 110 and a needle protector 10 are fixed together with a screw, as illustrated by FIG. 21; threads 20 and 130 of the needle protector 10 is locked in with threads of 132 and 114 of the catheter hub 110. After the catheter hub 110 is injected into the blood vessel of patients, one can only take apart the catheter hub 110 from needle protector 10 by turning both of them around, which is an unreliable and tedious process. As opposed to a one-dimensional pulling movement, on-spot revolution may very likely shake the needle tip and hence cause rupture in blood vessels.

Figures 2, 2A, 2B:
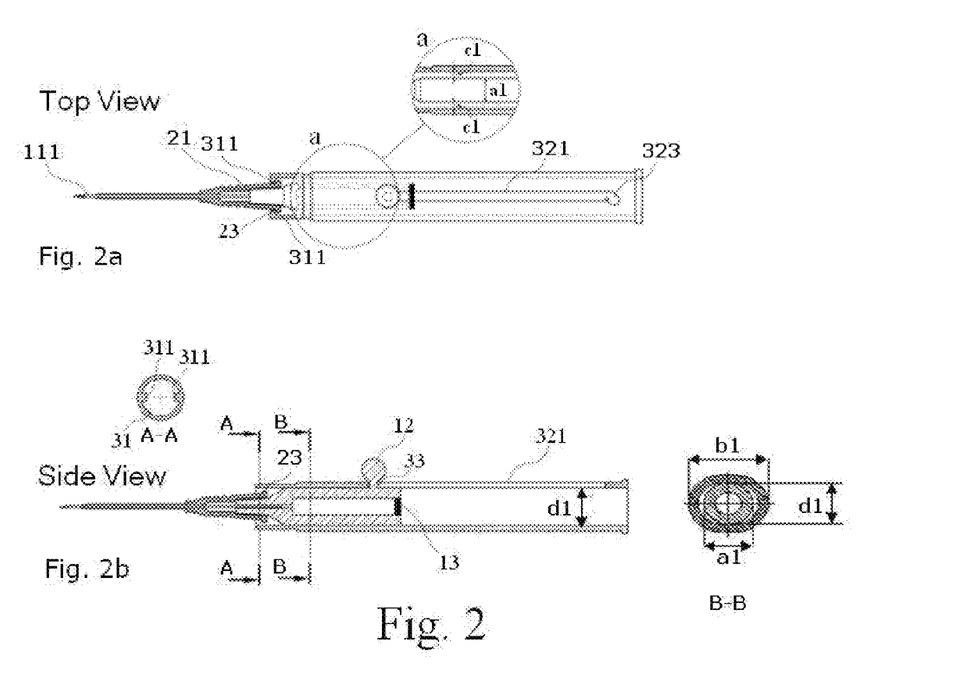
FIG. 2a is a top view of the first preferred embodiment.
FIG. 2b is a side view of the first preferred embodiment.

The present invention is also an improvement on U.S. Pat. No. 5,456,668, in which the slot is of a straight form throughout, without utilizing levering principle (the gravity of the syringe cover) to vertically rotate the syringe cover from its original central position, requiring device 65 in FIG. 8, a device 4 in FIG. 3, or a spring in syringe needle. When the injection needle is in the syringe cover, the shank 32 in FIG. 2 is breakable by manual operation to prevent the injection needle from being moved by the syringe needle back into the opening. The procedure needs two-handed operation.

SUMMARY OF THE INVENTION

The present invention, as opposed to the radially operating needle structure in U.S. Pat. No. 5,954,698, can only be operated axially in an X-axis dimension, or in a horizontal way; it, therefore, effectively reduces undesired shift of needle movement resulting from 360 degrees of radial movements.

The present invention, as opposed to U.S. Pat. No. 5,456,668, utilizes the fact that the gravity of the syringe cover is in the front when the fastening portion is at the rear end of sliding slot, so the syringe cover is vertically rotated. Another design is the sliding slot has a deflected slant portion at the distal end. When the fastening portion is at the deflected slant portion, the syringe needle is deflected laterally.

BRIEF DESCRIPTION OF THE DRAWINGS

The drawings disclose several illustrative embodiments of the present invention which serve to exemplify the various advantages and objects hereof, and are as follows.

DETAILED DESCRIPTION OF THE PREFERRED EMBODIMENT

Figure 1:
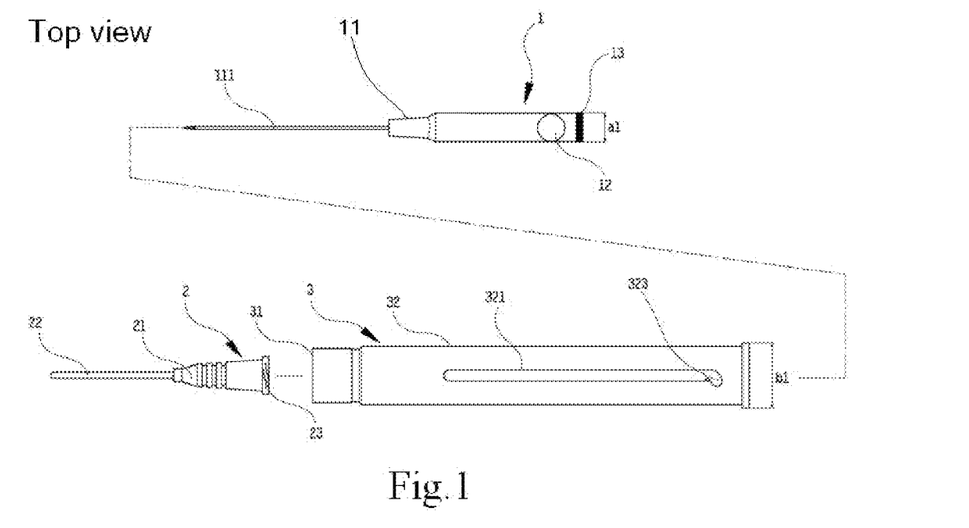
FIG. 1 is the first preferred embodiment.

Referring to FIG. 1, a retained needle structure of the present invention comprises a syringe needle 1, a catheter 2 and a syringe cover 3.

The syringe needle 1 has an inserting portion 11 at a front end. On the inserting portion 11 is inserted an injection needle 111. On the syringe needle 1, at least one fastening portion 12 is molded on one side and a ventilating filter 13 is at a rear end. The fastening portion 12 and syringe needle 1 is connected by a shank 33 (not shown in the figures).

The catheter 2 has a cannula 21 with a flexible tube 22. A stop portion 23 is disposed at an outer rim of a rear end of the cannula 21. The catheter 2 is sleeved on the inserting portion 11 of the syringe needle 1. The injection needle 111 of the syringe needle 1 is with the flexible tube 22 of the catheter 2. An opening 31 is disposed at the front end of syringe cover 3 with a hook portion 311 (not shown in the figure).

The syringe cover 3 has an aperture 31 formed at a front end. A plurality of hook portions 311, 312 are disposed at a front end of the syringe cover 3 (not shown in the figure). At least one gliding portion 32 extends on one side of the syringe cover 3 and corresponds to the fastening portion 12 of the syringe needle 1 in position and amount. On each of the gliding portions 32, a sliding slot 321 is disposed. The front end of the syringe cover has a connection member connected with a lid (not shown in the figure). A deflected slant portion 323 is formed at the distal end of the sliding slot 321.

Referring to FIG. 2, before using, the hook portion 311 of the syringe cover 3 connects with the stop portion 23 of the catheter 2; in the meantime, the fasten portion 12 of the syringe needle 1 is placed at the front end of the sliding slot 321 of the syringe cover 3, and the cannula 21 of the catheter 2 is fitted with the inserting portion 11 of the syringe needle 1.

Referring to the perspective top view of FIG. 2a, the syringe cover has an oval cross section, the diameter of the body of the syringe needle 1, a1, is smaller than the inner diameter (the major axis of the oval cross-section) of the syringe cover 3, b1, at the horizontal axis. Furthermore, there is a gap c1 between the diameter a1 and b1, as shown a (Enlarge View). The syringe needle 1 is in the frontal position of the syringe cover 3 now.

Figures 3, 3A, 3B:
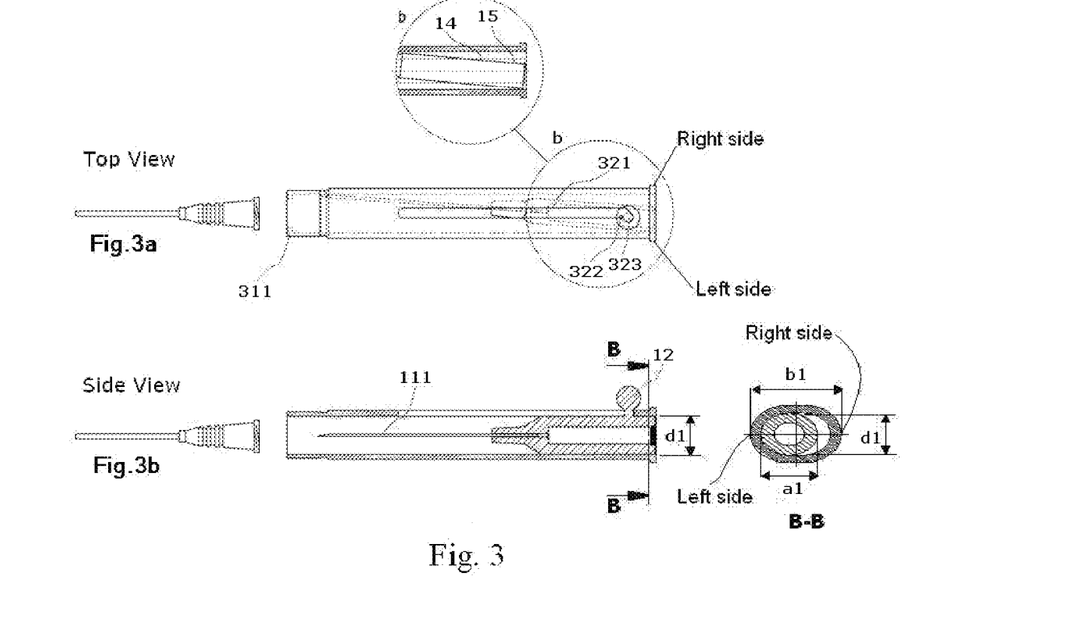
FIG. 3a is a top view of the first preferred embodiment after operation.
FIG. 3b is a side view of the first preferred embodiment after operation.

Referring to the perspective side view of FIG. 3b, the diameter of the body of the syringe needle 1 is d1 which coincides completely with the inner diameter (the minor axis of the oval cross-section) of the syringe cover 3 at the vertical axis. It does not have any gap between them as illustrated in B-B section. The longitudinal axis of the injection needle 111 is coaxial with the longitudinal axes of the syringe needle 1 and the syringe cover 3.

The injection needle 111 penetrates the skin and vein of the patient and guides the catheter 2 into the vein. At the same time, the catheter 2 moves forward. Because a plurality of hook portions 311,312 as illustrated in A-A section are disposed at a front end of the syringe cover 3, they also connect with the catheter 2 by the stop portion 23. So the stop portion 23 of the catheter 2 moves syringe cover 3 forward, Once the catheter is in position, the fastening portion 12 of the syringe needle 1 is withdrawn along the sliding slot 321 of the syringe cover 3. When fastening portion 12 enters the slant portion 323, the injection needle 111 is already inside of the syringe cover 3. It means the injection needle 111 is located at the back of the hook portion 311. At the same time, the stop portion 23 of catheter 2 is disconnected from hook portion 311 of syringe cover 3 (FIG. 3). As shown by FIG. 3a, at this time, body of the syringe needle 1 is no longer in the center position of syringe cover 3, but is deflected from the center; as a result, the injection needle 111 is deflected from center position too. Finally, the injection needle 111 shifts to the right and behind the hook portion 311 of the syringe cover 3. A salient 322, positioned at the rear end of the sliding slot 321 or on slant portion 323, bars forward movement of the fastening portion 12 when the fastening portion 12 enters the slant portion 323. It is very difficult to exposes the injection needle 111 outside of the syringe cover 3. In FIG. 3a, the number 14 refers to the location of the syringe needle 1 in the sliding slot 321 without deflection, and the number 15 refers to the location of the syringe needle 1 in the slant portion 323, as shown b (Enlarge view).

Further referring to the side view of FIG. 3b, the syringe needle 1 is still in the center of the syringe cover 3 at the vertical axis. It means that the injection needle 111 deflects to the right side at horizontal direction and sits behind the hook portion 311 of the syringe cover 3. We also can see the syringe needle deflects to the left side as shown in B-B section view.

Figure 4:
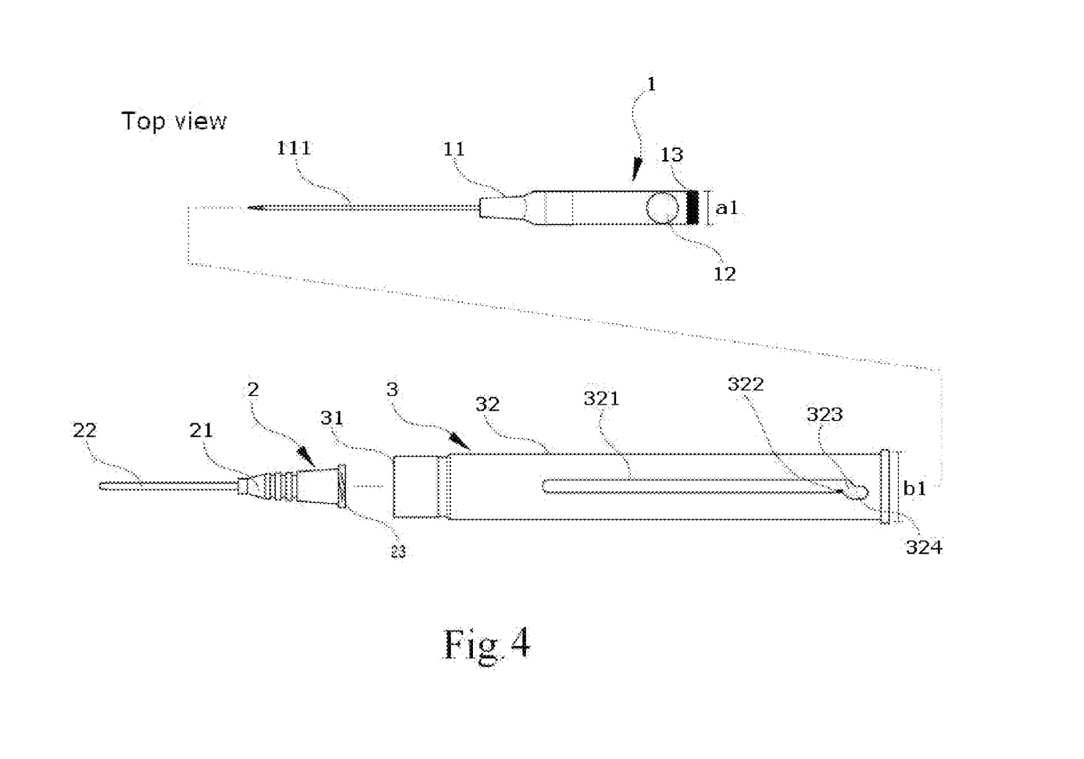
FIG. 4 further illustrates the first preferred embodiment.

Further referring to FIG. 4, a reception slot 324 is disposed at the rear end of the slant potion 323 of the syringe cover 3, which provides an extended protection when syringe needle 1 enters reception slot 324; i.e. the injection needle 111 would not be exposed outside of syringe cover 3.

Figure 5:
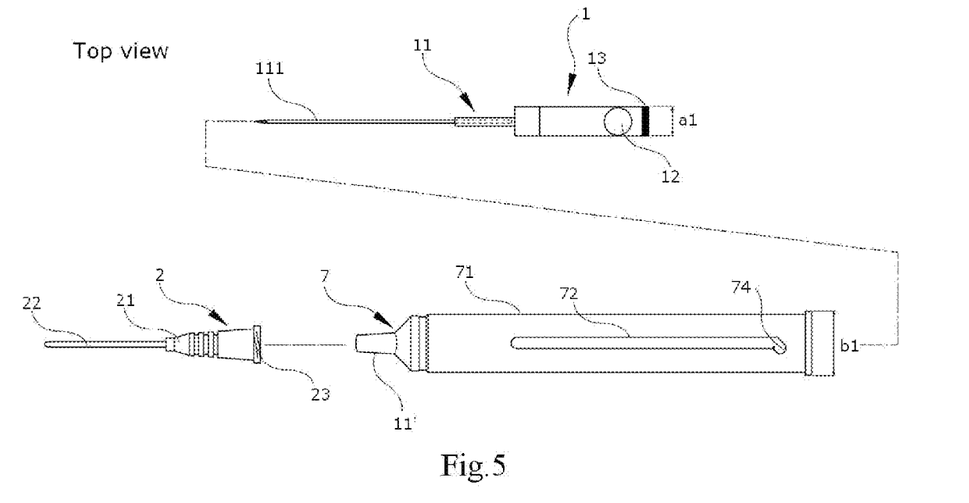
FIG. 5 is the second preferred embodiment.

Further referring to FIG. 5, a safe catheter structure is composed of a syringe needle 1, catheter 2 and a syringe cover 7. The syringe needle 1 has an inserting portion 11 at a front end. On the inserting portion 11 is inserted an injection needle 111. On the syringe needle 1, at least one fastening portion 12 is molded on one side and a ventilating filter 13 is at its rear end. The fastening portion 12 and syringe needle 1 is connected by a shank 33 (not shown in the figure).

The catheter 2 has a cannula 21 with a flexible tube 22. A inserting portion 11' formed at a front of the syringe cover 7. At least one gliding portion 72 extends at an outer rim of the syringe cover 7, and corresponds to the fastening portion 12 of the syringe needle 1 in position and amount. On each of the gliding portions 71, a sliding slot 72 is disposed. A deflected slant portion 74 is formed at the distal end of the sliding slot 72. Referring to the top view of FIG. 5, the diameter of body of the syringe needle 1, a1, is smaller than the inner diameter b1 of the syringe cover 7 at horizontal axis.

Syringe cover 7 meets with the insertion portion 11 of the syringe needle 1, while catheter 2 meets with inserting portion 11' of syringe cover 7 via the cannula 21. Injection needle 111 enters catheter 2 through syringe cover 7. The snug friction between the cannula 21 of catheter 2 and the inserting portion 11' of the syringe cover 7 lets syringe cover 7 move with catheter 2. Also, fastening portion 12 of syringe needle 1 moves freely along the sliding slot 72 of the syringe cover 7.

Figures 6, 6A, 6B:
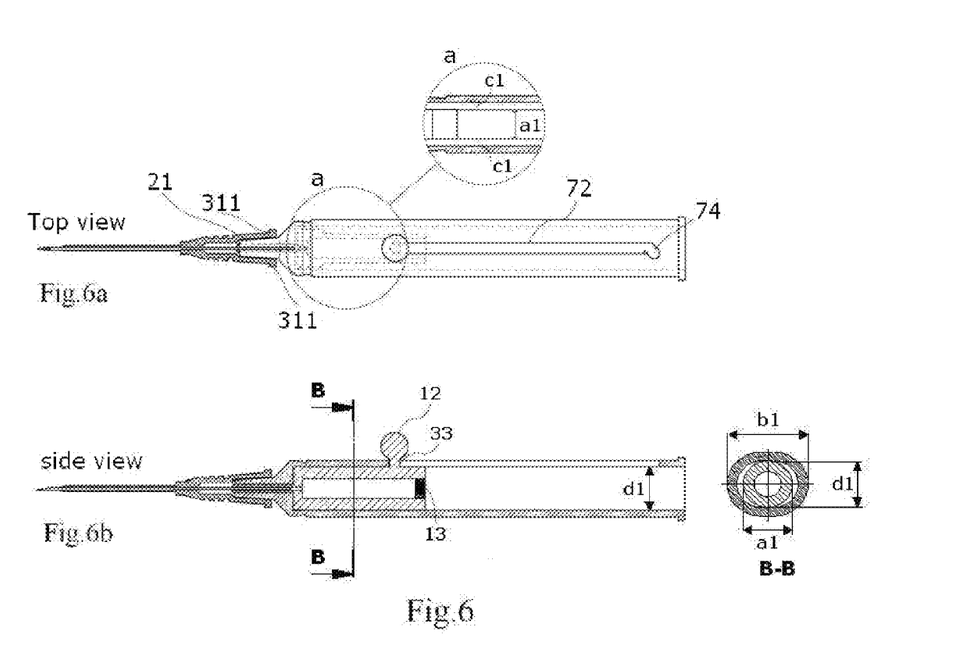
FIG. 6a is a top view of the second preferred embodiment.
FIG. 6b is a side view of the second preferred embodiment.

Referring to the top view of FIG. 6a, the diameter of body of the syringe needle 1, a1, is smaller than the inner diameter b1 of the syringe cover 7 at horizontal axis; hence, there is a gap c1 between a1 and b1. Syringe needle 1 is positioned in the center of syringe cover 7. The syringe needle 1 is in the front position of the syringe cover 7 now. Referring to the side view of FIG. 6b, the outer diameter of body of syringe needle 1, d1, coincides with the inner diameter of syringe cover 7 at the vertical axis, and does not allow having gap between them as illustrated B-B section. The longitudinal axis of the injection needle 111 is coaxial with the longitudinal axes of the syringe needle 1 and the syringe cover 7.

Then the injection needle 111 penetrates the skin and vein of the patient and guides the catheter 2 into the vein. At the same time, the catheter 2 moves forward. The cannula 21 of catheter 2 makes a snug friction fit over the inserting portion 11' of the syringe cover 7. If the syringe cover 7 has one hook at the frontel and the catheter 2 has a stop portion disposed on an outer rim of the cannula (not shown in the figures). The hook portion of the syringe cover 7 connects to the stop portion of the catheter 2 (not shown in the figures). Then the user can operate more reliable. When catheter 2 moves forwards into the vessel, syringe cover 7 moves forward too; in the meantime, fastening portion 12 moves backwards along the sliding slot 72 of syringe cover 7.

When fastening portion 12 enters slant portion 74, the injection needle 111 is already inside of syringe cover 3 and at the back of inserting portion 11'.

Figures 7, 7A, 7B:
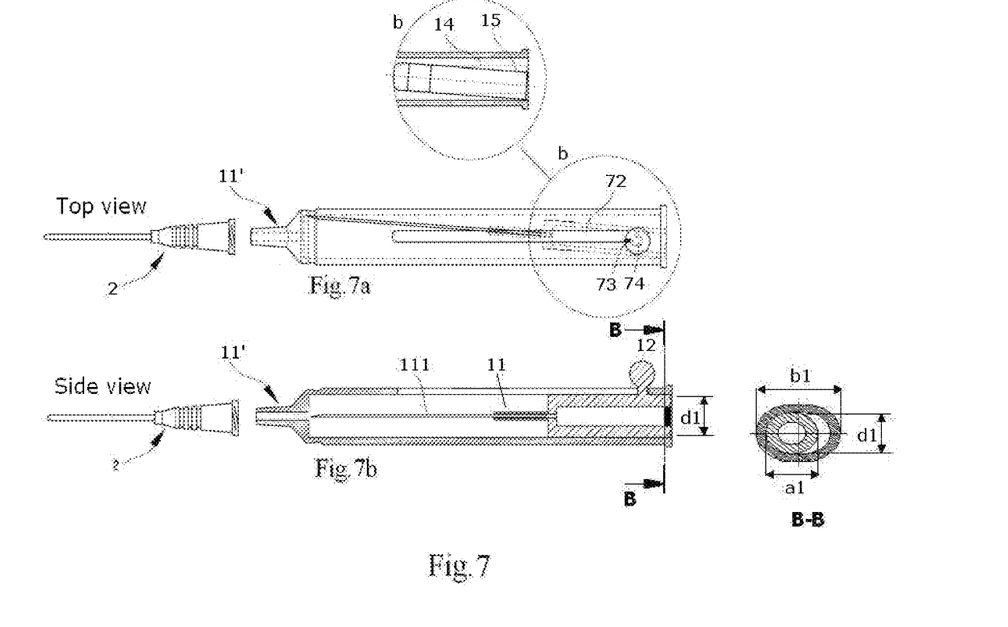
FIG. 7a is a top view of the second preferred embodiment after operation.
FIG. 7b is a side view of the second preferred embodiment after operation.

As shown by FIG. 7a, body of syringe needle 1 is not at the center of syringe cover 7 but is deflected to the right side at horizontal direction. A salient 73 is disposed either at the rear end of sliding slot 72 or on slant portion 74. The salient 73 prevents fastening portion 12 to move forward when the fastening portion 12 enters slant portion 74. It is very difficult for injection needle 111 to exposed outside of syringe cover 3. In FIG. 7a, numeral 14 denotes the position of syringe needle 1 at sliding slot 72 without deflection; numeral 15 denotes the position of syringe needle 1 at slant position 74, while injection needle 111 is already deflected from the center of syringe cover 7.

In the side view of FIG. 7b, body of syringe needle 1 is still at the center of syringe cover 7 at the vertical axis; i.e.

injection needle 111 is deflected to the right side at horizontal direction and sits behind inserting portion 11' of syringe cover 7. We also can see the syringe needle 1 deflects to the left side as shown in B-B section view.

Figure 8:
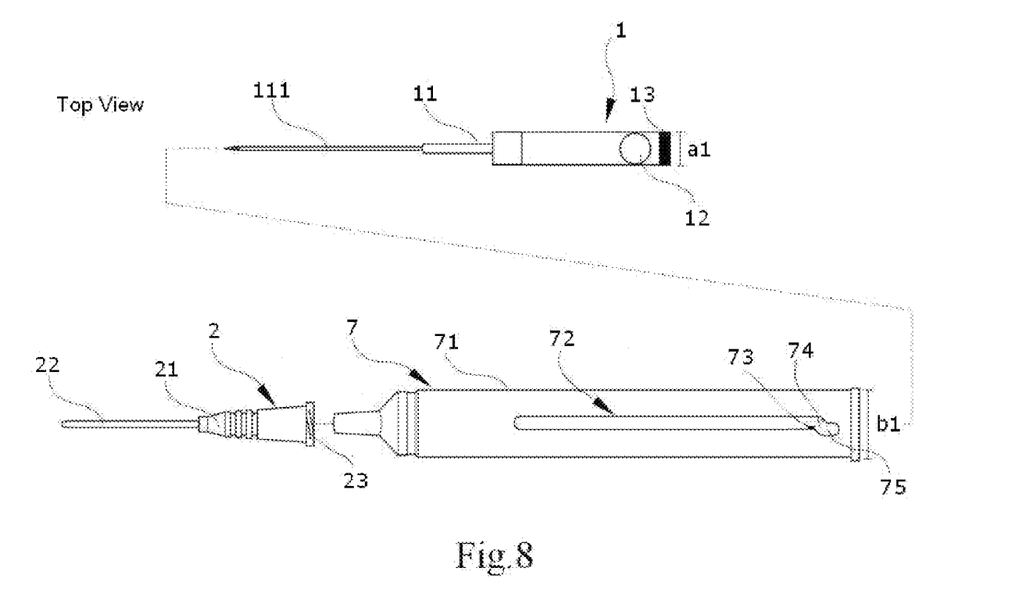
FIG. 8 further illustrates the second preferred embodiment.

Further referring to FIG. 8, a reception slot 75 is disposed at the rear end of slant portion 74 of syringe cover 7 to secure the syringe needle 1 in position when syringe needle 1 enters reception slot 75.

Figure 9:
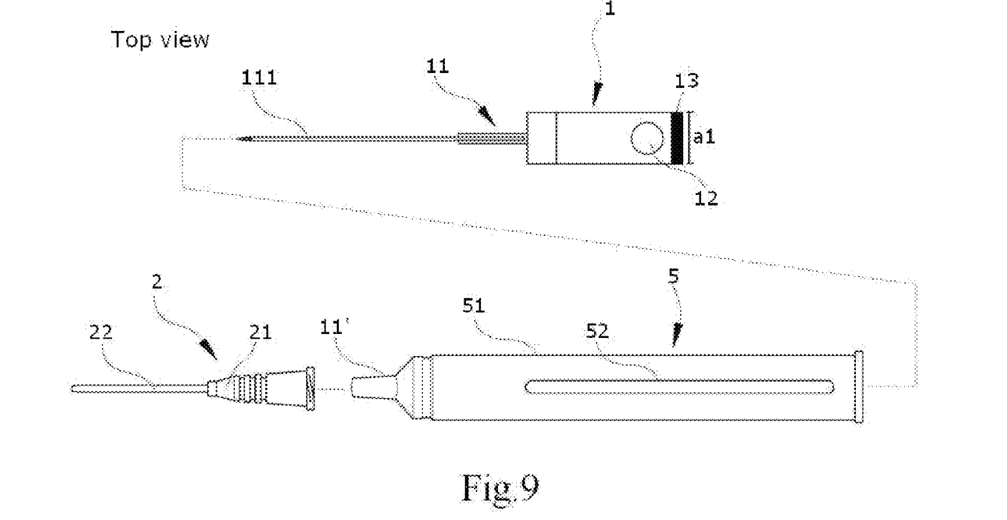
FIG. 9 is the third preferred embodiment.

The latest design refers to FIG. 9, the safety catheter structure consists of a syringe needle 1, catheter 2, and syringe cover 5. An injection needle 111 is disposed at the front end of syringe needle 1 and ventilating filter 13 is inserted, while a fastening portion 12 is disposed on one side of catheter 2. A flexible tube 22 is disposed at the front end of cannula 21 of catheter 2. An inserting portion 11' is at the front end of syringe cover 5, and a sliding slot 52 on gliding portion 51 of syringe cover 5.

Figures 10, 10A, 10B:
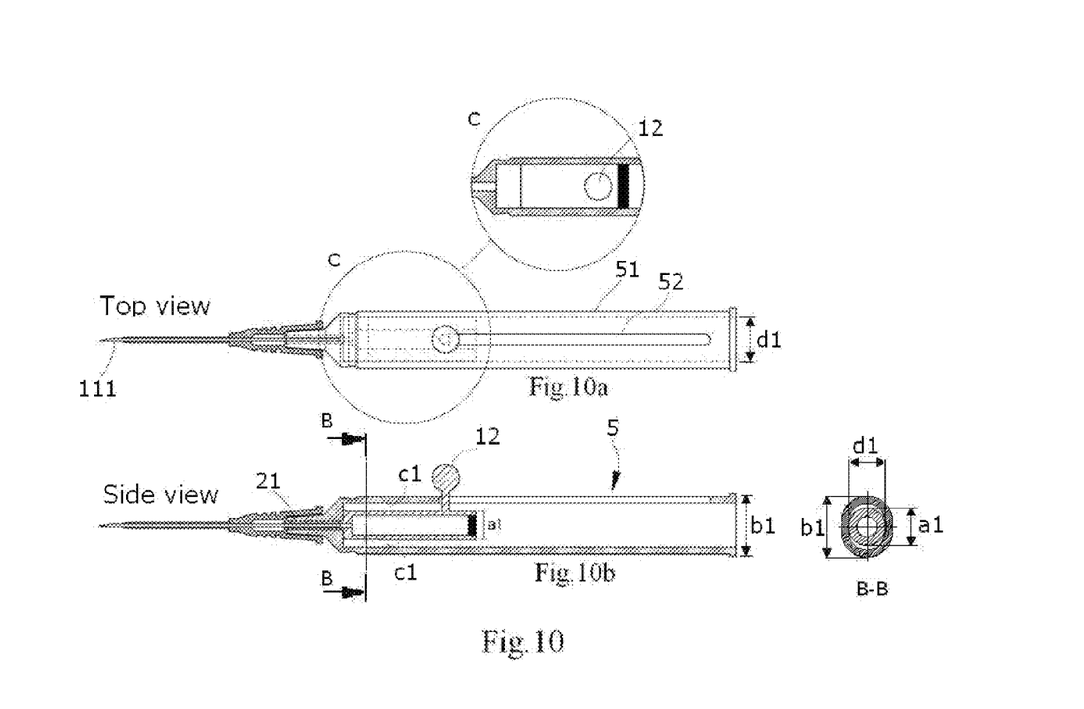
FIG. 10a is a top view of the third preferred embodiment.
FIG. 10b is a side view of the third preferred embodiment.

Further referring to FIG. 10, syringe cover 5 connects via inserting portion 11' with inserting portion 11 of syringe needle 1, while catheter 2 connects via cannula 21 with inserting portion 11' of syringe cover 5. Injection needle 111 of syringe needle 1 enters catheter 2 through syringe cover 5.

Syringe cover 5 moves with catheter 2 by the snug friction between cannula 21 of catheter 2 and inserting portion 11' of syringe cover 5. Under the same process, fastening portion 12 of syringe needle 1 moves freely in the sliding slot 52 of syringe cover 5. The top view of FIG. 10a shows that the outer diameter of body of syringe needle 1, d1, coincides completely with the inner diameter of syringe cover 5, and does not having gap between them, as shown c (Enlarge view). The side view of FIG. 10b shows that the diameter of body of syringe needle 1, a1, is smaller than the inner diameter b1 of syringe cover 5 at the vertical axis, making a gap c1 between them. When it is not in use, therefore, syringe needle 1 is positioned at the front of syringe cover 5. If the syringe cover 5 has at least one hook at the frontel and the catheter has a stop portion disposed on an outer rim of the cannula (not shown in the figures). The hook portion of the syringe cover 5 connects to the stop portion of the catheter 2. (not shown in the figures). Then the user can operate more reliable.

Figures 11, 11A, 11B:
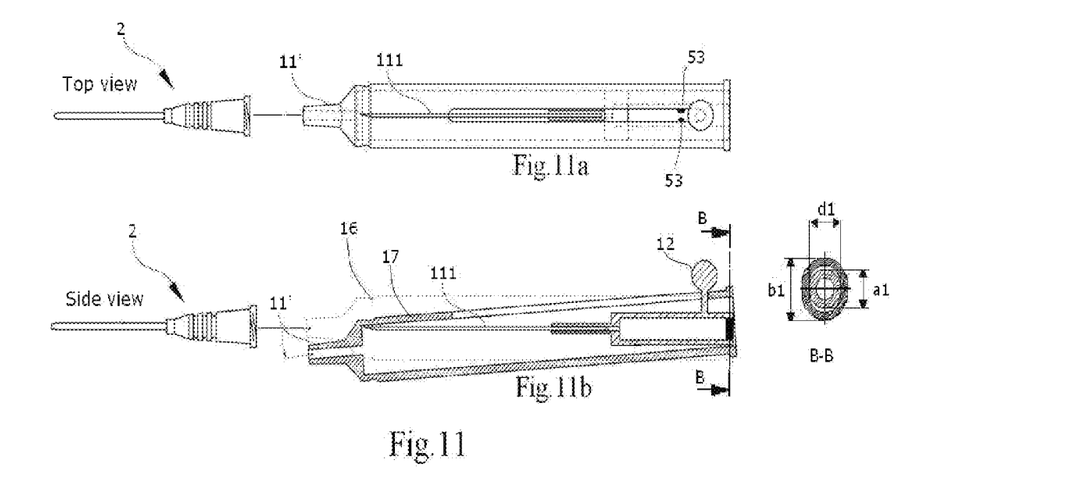
FIG. 11a is a top view of the third preferred embodiment of the present invention after operation.
FIG. 11b is a side view of the third preferred embodiment of the present invention after operation.

When catheter 2 moves forward into the vessel, syringe cover moves forward too; in the meantime, fastening portion 12 of syringe needle 1 moves backward along the sliding slot 52 of syringe cover 5. When injection needle 111 enters syringe cover 5 and sits behind inserting portion 11', catheter 2 is separated with syringe cover 5 (FIG. 11). Since fastening portion 12 of syringe needle 1 is already positioned at the right rear end of sliding slot 52 of syringe cover 5, injection needle 111 is situated in the syringe cover 5, as shown by FIG. 11a. In contrast, FIG. 11b shows that syringe cover 5 is vertically rotated down from its original center position, making injection needle 111 positioned at the back of inserting portion 11' and tilted upwards, due to the gravity of syringe cover 5 is located at the front and the levering effect from gravity center makes syringe cover 5 rotating down; as a result, the position of syringe needle 1 rotates, and makes injection needle 111 moves forward impossibly. Preferrably, a salient 53 is positioned at the rear end of sliding slot 52 of syringe cover 5, which would increase its safety in use when fastening portion 12 of syringe needle 1 is positioned at the back of salient 53. In FIG. 11b, numeral 16 denotes the position of syringe cover 5 at original position; numeral 17 denotes the position of syringe needle 1 at the right rear end of slide slot, while signal cover 5 is already rotation down.

Figures 12, 12A, 12B:
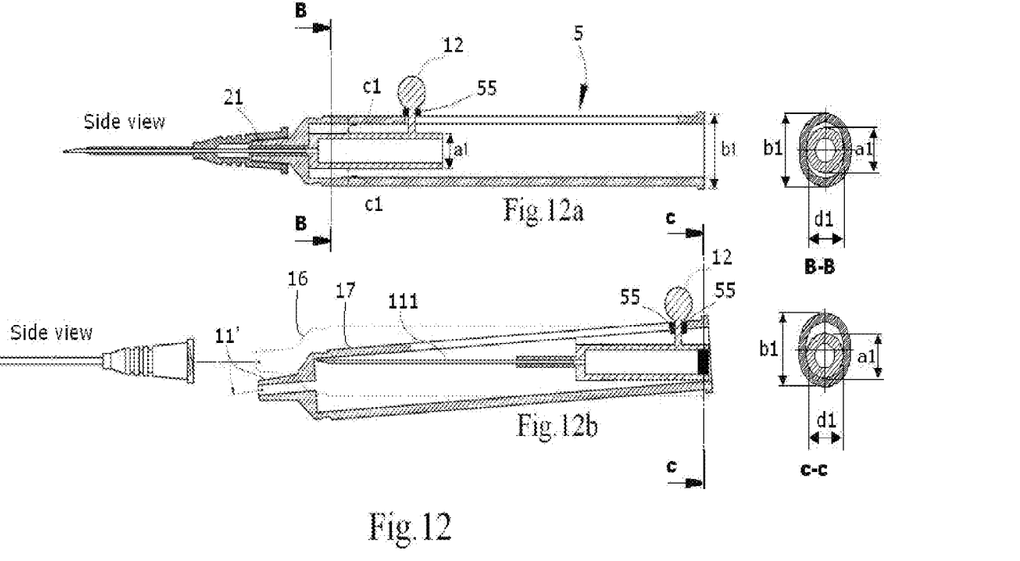
FIG. 12 further illustrates the third preferred embodiment.

Further referring to FIG. 12a, a salient 55 is positioned below fastening portion 12 of syringe needle 1. When fastening portion 12 moves to the right rear end of sliding slot 52, the levering effect from gravity of the syringe cover makes the syringe cover 5 rotating down. Then the user vertically pushes the fastening portion 12 to let the salient 55 into the sliding slot 12, which would increase its safety in use, as shown by FIG. 12b. FIG. 12b shows that syringe cover 5 is vertically rotated down from its original center position.

Many changes and modifications in the above the described embodiment of the invention can, of course, be carried out without departing from the scope. Accordingly, to promote the progress in science and the useful arts, the invention will be disclosed and intended to be limited only by the scope of the appended claims.

The invention claimed is:

1. A retained needle structure, comprising:
 a syringe needle comprising an inserting portion at a front end of a syringe body, an injection needle inserted on the inserting portion, and a fastening portion at one side of the syringe body; and
 a syringe cover comprising an aperture at a proximal end and a gliding portion extending at one side, wherein the gliding portion includes a sliding slot that forms a deviates slant portion at a distal end of the syringe cover, wherein the syringe cover has an oval cross section having a major axis and a minor axis,
 wherein the fastening portion of the syringe needle is configured to move along the sliding slot of the syringe cover, and
 wherein the width of the minor axis of the syringe cover coincides with a diameter of the syringe body and the width of major axis of the syringe cover is larger than an outer diameter of the syringe body such that a clearance exists between the syringe cover and the syringe body, thereby, when the fastening portion enters the deviates slant portion, and the injection needle is retracted inside the syringe cover, the syringe needle can be deflected to a position not aligned with a central axis of the syringe cover.

2. The retained needle structure as claimed in claim 1, wherein a rear end of the sliding slot or the deviated slant portion has a salient.

3. The retained needle structure as claimed in claim 1, where the deviated slant portion includes a reception slot at one end of deviated slant portion.

4. A retained needle structure, comprising:
 a syringe needle comprising an inserting portion on a front end of a syringe body, an injection needle inserted on the inserting portion, and a fastening portion on one side of the syringe body,
 a syringe cover comprising a gliding portion extending at one side, wherein the gliding portion of the syringe cover includes a sliding slot, and the syringe cover has an oval cross section having a major axis and a minor axis,
 wherein the syringe cover is sleeved on a front end of the syringe needle, and
 wherein the width of the minor axis of the syringe cover coincides with a diameter of the syringe body and the width of major axis of the syringe cover is larger than an outer diameter of the body of the syringe needle such that a clearance exists between the syringe cover and the syringe body, thereby, when the injection needle is retracted inside the syringe cover, the syringe needle is deflected to a position not aligned with a central axis of the syringe cover.

5. The retained needle structure as claimed in claim 4, further comprising a deviated slant portion formed at a distal end of the sliding slot.

6. The retained needle structure as claimed in claim 5, wherein a rear end of the sliding slot or the deviated slant portion has a salient.

7. The retained needle structure as claimed in claim 4, further comprising a catheter comprising a cannula having a flexible tube, wherein a stop portion on an outer rim of the cannula is configured to connect with the syringe cover.

8. A retained needle structure, comprising:
 a syringe needle comprising an inserting portion at a front end of a syringe body, an injection needle inserted on the inserting portion, and a fastening portion at one side of the syringe barrel; and
 a syringe cover comprising a gliding portion extending at one side, the gliding portion of the syringe cover has a sliding slot, the syringe cover having an oval cross section having a major axis and a minor axis,
 wherein the syringe cover is sleeved on the front end of the syringe needle and the syringe needle runs through the syringe cover, the fastening portion of the syringe needle is received within the sliding slot of the syringe cover, and
 wherein the width of the minor axis of the syringe cover coincides with the diameter of the syringe body and the width of the major axis of the syringe cover is larger than an outer diameter of a body of the syringe needle such that a clearance exists between the syringe cover and the syringe body, thereby, when the fasting portion is at the rear end of the sliding slot, and the injection needle is retracted inside the syringe cover, the syringe cover can drop down due to gravity acting on the syringe cover, relative to the syringe needle, such that the syringe needle is not aligned with a central axis of the syringe cover.

9. The retained needle structure as claimed in claim 8, wherein a rear end of the sliding slot has a salient.

10. The retained needle structure as claimed in claim 8, wherein a salient is positioned below the fastening portion of the syringe needle.

* * * * *